United States Patent [19]

Harman et al.

[11] Patent Number: 5,360,608
[45] Date of Patent: Nov. 1, 1994

[54] **FUNGICIDAL COMPOSITIONS COMPRISING CHITINASE AND *ENTEROBACTER CLOACAE*, AND A METHOD FOR STIMULATION PROLIFERATION OF *E. CLOACASE***

[75] Inventors: Gary E. Harman; Matteo Lorito; Christopher K. Hayes, all of Geneva, N.Y.

[73] Assignee: Cornell Research Foundation, Inc., Ithaca, N.Y.

[21] Appl. No.: 12,945

[22] Filed: Feb. 3, 1993

[51] Int. Cl.$^5$ ................... A01N 63/00; C12N 1/38; C12N 1/20; C12N 9/24
[52] U.S. Cl. ................ 424/94.61; 424/93 P; 435/244
[58] Field of Search ............ 424/94.61, 93 P, 405; 435/252.1

[56] References Cited

U.S. PATENT DOCUMENTS

| | | | |
|---|---|---|---|
| 4,751,081 | 6/1988 | Suslow et al. | 424/93 A |
| 4,940,840 | 7/1990 | Suslow et al. | 500/205 |
| 5,173,419 | 12/1992 | Harman et al. | 435/209 |
| 5,290,687 | 3/1994 | Suslow et al. | 435/69.1 |

OTHER PUBLICATIONS

Gunner, H. B., et al, U.S. Forest Serv. GTR-NE-100, pp. 102-108 (1985).
Hadar, Y., et al, *Phytopathology* 73:1322-1325 (1983).
Harman, G. E., et al, Proceedings of EFPP/IOBC Workshop, Copenhagen, Denmark, Jul. 1991, 8 pages.
Klemsdal, S. S., et al, 11th Nordic Postgraduate School in Plant Pathology, abstract of poster presented Feb. 3, 1992 in Tisvildeleije, Denmark.
Jarosz, J., et al, Comp. Biochem. Physiol., vol. 87A, No. 1, pp. 189-192 (1987).
Kwok, O. C. H., et al, Phytopathology 77:1206-1212 (1987).
Lorito, M., et al, Phytopathology, 82, No. 2, 245-246 (Feb. 1992).
Morris, O. N., The Canadian Entomologist, vol. 108, No. 3, 225-233 (Mar. 1976).
Nelson, E. B., et al, Phytopathology 76:327-335 (1986).
Richer, D. L., Pestic. Sci. 19: 309-315 (1987).
Roberts, D. P., et al, Phytopathology 80, 461-465 (1990).
Roberts, D. P., et al, Canadian J. Microbiol. 37:168-170 (1991).
Shapiro, M., et al, Journal of Economic Entomology, vol. 80, No. 6, 1113-1116 (Dec. 1987).
Smirnoff, W. A., The Canadian Entomologist, 103:1829-1831 (1971).
Smirnoff, W. A., Journal of Invertebrate Pathology, 21, 116-118 (1973).
Vessey, J. C., et al, Trans. Br. Mycol. Soc. 60:710-713 (1973).
Tronsmo, A., Biological Control 1, 59-62 (1991).
Cherif et al., Biol. Abstracts 96(1):9470 (1993).
Wisniewski, M. et al., Can. J. Botany 67:2317-2323 (1989).
Lorito, M. et al.; Phytopathology 83:302-307 (1993).

*Primary Examiner*—Robert A. Wax
*Assistant Examiner*—Eric Grimes

[57] ABSTRACT

Combination of fungal cell wall degrading enzymes (e.g., chitinolytic enzymes) and antifungal bacteria (e.g., *E. cloacae*) which bind to fungal cell walls in the presence of said enzymes even when sugars are present, increases potency and range of use of the bacteria and fosters proliferation thereof.

12 Claims, 4 Drawing Sheets

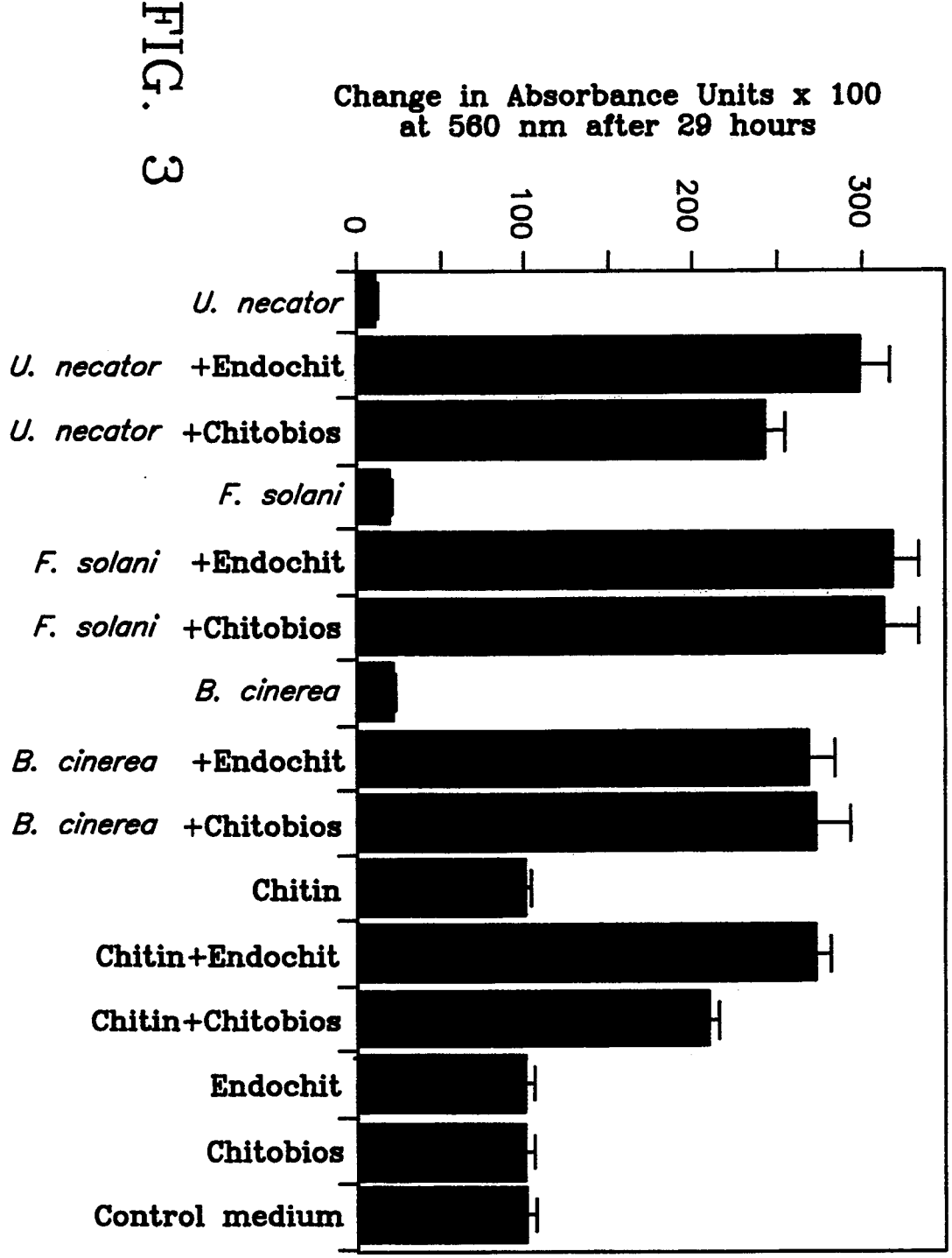

FUNGICIDAL COMPOSITIONS COMPRISING CHITINASE AND *ENTEROBACTER CLOACAE*, AND A METHOD FOR STIMULATION PROLIFERATION OF *E. CLOACASE*

This invention was made in part with Government support under U.S.-Israel Binational Agricultural Research and Development Fund (BARD) grant number US-1723-89. The Government has certain rights in the invention.

TECHNICAL FIELD

This invention is directed at antifungal synergistic combinations of fungal cell wall degrading enzyme and fungal cell wall binding antifungal bacteria and use thereof for topical application in agriculture to inhibit replication, germination or growth of fungi and to a method of proliferating the growth of antifungal bacteria.

1. Background of the Invention

Various antifungal bacteria are known, e.g., *Enterobacter cloacae*, *Pseudomonas fluorescens* and *Pseudomonas putida*. The biocontrol ability of *Enterobacter cloacae* has been associated with its ability to bind to hyphal walls. It has been reported that some sugars such as D-glucose and sucrose inhibit this binding. Consequently, *E. cloacae* has been able only to protect seeds and plants with low sugar exudation.

2. Summary of the Invention

It is an object of this invention to increase the potency of bacteria where antifungal function is associated with ability to bind to fungal cell walls and to expand the range of use of such bacteria so that antifungal function occurs even when normally interfering sugars are present.

The antifungal composition of the invention herein comprises (a) purified fungal cell wall degrading enzyme, and (b) antifungal bacteria which bind to fungal cell walls in a 2% dextrose aqueous solution in the presence of enzyme (a) but which do not bind to fungal cell walls in a 2% dextrose aqueous solution in the absence of enzyme (a), these being present in a ratio of (b) to (a) ranging from 1 cell of (b) to 1 μg of (a) to 200,000 cells of (b) to 1 μg of (a), the combination of (a) and (b) being present in an antifungal effective amount.

A method of the invention herein is directed to inhibiting the replication, germination or growth of a fungus and comprises contacting such fungus or a locus to be protected from such fungus, with an antifungal effective amount of composition of the invention herein.

A method of another embodiment of the invention herein is directed to causing proliferation in the growth of *Enterobacter cloacae* and comprises the steps of reacting fungal cell wall degrading enzyme with a substrate therefor to obtain a nutrient for *Enterobacter cloacae* and growing *Enterobacter cloacae* in the presence of said nutrient so as to cause said proliferation.

The term "fungal cell wall degrading enzyme" is used herein to mean enzyme that effects lysis of fungal cell walls.

The term "purified fungal cell wall degrading enzyme" is used herein to mean cell wall degrading enzyme which is purified to a specific activity greater than its specific activity in a culture filtrate of the microorganism from which it is obtained and thus distinguishes the case where bacteria exude cell wall degrading enzymes in nature.

The term "antifungal bacteria" is used herein to mean bacteria which inhibit the replication, germination or growth of a fungus.

The term "bind to fungal cell walls" is used herein to mean physical attachment of bacteria to fungi.

The term "inhibit" is used herein to mean reduce the growth and/or development of fungi compared to where inhibiting agent is not present.

The term "locus to be protected from such fungus" includes seeds, roots, stems, leaves, flowers and fruits to be protected and to the soil surrounding seeds and roots to be protected.

The term "causing proliferation in the growth of" is used herein to mean increasing the number of bacterial cells at least five-fold compared to where fungal cell wall degrading enzyme or substrate therefor is not present.

The term "growing *Enterobacter cloacae*" is used herein to include not only culturing but replication in nature.

BRIEF DESCRIPTION OF THE DRAWINGS

FIG. 3 is a set of bar graphs depicting change in absorbance for various substrates and enzymes and sets forth results for Example III.

DETAILED DESCRIPTION

Figure 1A:
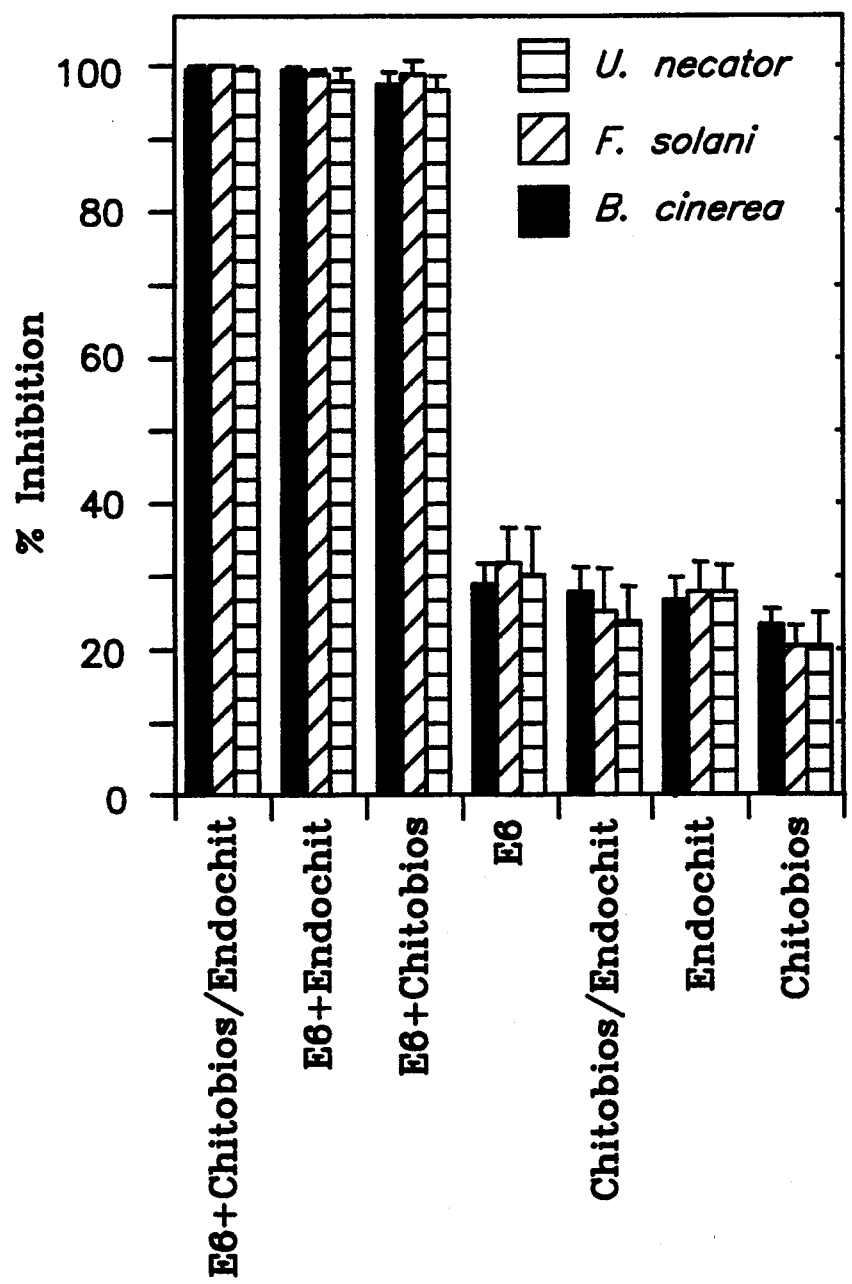
FIG. 1A is a set of bar graphs depicting percent inhibition of spore germination for various treatments of three fungi and sets forth results for Example I.

The fungal cell wall degrading enzymes for the compositions herein include, for example, chitinolytic enzymes and β-1,3-glucanolytic enzymes for degrading cell walls of fungi where the cell walls contain, as major structural components, chitin and β-1,3-glucans, and cellulases for degrading cell walls of lower fungi (Oomycetes) where the cell walls contain, as a major structural component, cellulosic polysaccharides.

These enzymes are found in fungi, bacteria and higher plants. The compositions herein are limited to containing purified enzymes to distinguish the case where bacteria exude cell wall degrading enzymes in nature. The purified enzymes can be partially purified, i.e., purified compared to what occurs in nature or in a culture filtrate of the microorganism from which it is obtained, but with other protein present. However, the enzyme component of the composition herein is preferably used in biologically pure form, that is, purified to be free of contaminating protein (purified to homogeneity). Fungal cell wall degrading enzymes are readily obtained in biologically pure form from source microorganisms by culturing the source microorganism, concentrating the culture filtrate, fractionating by gel filtration chromatography, concentrating, and further purifying by chromatofocusing, followed, if necessary, by isoelectrofocusing in a Rotofor cell (BioRad, Richmond, Calif.).

The chitinolytic enzymes cleave chitin, and include, for example, endochitinases, chitin 1,4-β-chitobiosidases and N-acetyl-β-D-glucosaminidases. These can be obtained from fungi, for example, from the genera Trichoderma, Gliocladium, Lycoperdon and Calvatia; from bacteria, e.g., from the genera Streptomyces, Vibrio, Serratia and Bacillus; and from higher plants, e.g., Nicotiana, Cucumis and Phaesolus.

The endochitinases are enzymes that randomly cleave chitin. Endochitinase activity is readily measured by determining optical density at 510 nm as reduction of turbidity of a 1% suspension of moist purified colloidal chitin in 100 mM sodium acetate buffer, pH 5.5, or in 50 mM $KHPO_4$ buffer, pH 6.7, after 24 hours of incubation at 30° C. For calculation of specific activity, one unit is defined as the amount of enzyme required to obtain a 5% turbidity reduction.

A very preferred endochitinase is isolated from *Trichoderma harzianum* strain P1 having accession No. ATCC 74058 and has a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of molecular weight of standard proteins) and an isoelectric point of 3.9 as determined by isoelectric focusing electrophoresis from a regression of distance versus the isoelectric point of standard proteins. The specific activity of the purified endochitinase was determined to be 0.86 units/μg protein with the turbidity reducing assay and 2.2 nkatal/μg protein when nitrophenyl-β-D-N,N',N''-triacetylchitotriose was used as a substrate. The production and purification to homogeneity of this endochitinase are described in Harman et al U.S. Pat. No. 5,173,419, and also in Ser. No. 07/919,784, filed Jul. 27, 1992.

Another endochitinase is isolated from *Gliocladium virens* strain 41 having accession No. ATCC 20906 and has a molecular weight of 41 kDa (as determined by sodium dodecyl sulfate polyacrylamide gel electrophoresis after the protein was prepared under reducing conditions, from a regression based on the log of molecular weight of standard proteins) and an isoelectric point of 7.8 as determined by isoelectric focusing from a regression of distance versus the isoelectric point of standard proteins. The procedures used for molecular weight determination and isoelectric point determination are the same as those described in detail in Ser. No. 07/919,784. The enzyme is active in citric acid/$K_3PO_4$ buffer over a pH range of 3.5 to 7.0 and shows a 90-100% activity between pH 4.0 and 6.0 and shows maximum activity at pH 4.5. The optimum temperature for endochitinase activity at pH 5.5 is between 30° and 37° C., and activity drops off sharply at temperatures above 40° C. The production and purification to homogeneity of this enzyme are described in detail in the patent application of Harman et al, Ser. No. 07/990,609, filed on Dec. 15, 1992. The enzyme was purified to an activity 105-fold that of its activity in the culture filtrate.

The chitin 1,4-β-chitobiosidases cleave dimeric units from chitin from one end, i.e. cleave chitobiose units from chitin. Chitin 1,4-β-chitobiosidases are sometimes referred to for convenience hereinafter as chitobiosidases. Chitobiosidase activity is readily determined by measuring the release of p-nitrophenol from p-nitrophenyl-β-D-N,N'-diacetylchitobiose, e.g., by the following procedure. A substrate solution is formed by dissolving 3 mg of substrate in 10 ml 50 mM $KHPO_4$ buffer, pH 6.7. Fifty μl of substrate solution is added to a well in a microtiter plate (Corning). Thirty μl of test solution is added, and incubation is carried out at 50° C. for 15 minutes. Then the reaction is stopped by the addition of 50 μl of 0.4M $Na_2CO_3$, and the optical density is read at 410 nm. An activity of one nanokatal (nkatal) corresponds to the release of 1 nmol nitrophenol per second.

A chitobiosidase is isolated from Trichoderma harzianum strain P1 having accession No. ATCC 74058 and in its most prevalent form has a molecular weight of 36 kDa (as determined by sodium dodecyl sulfate polyacrylamide gel electrophoresis after the protein was prepared under reducing conditions, on direct comparison to migration of a 36 kDa protein), and an isoelectric point of 4.4±0.2 as determined based on its elution profile from a chromatofocusing column and a molecular weight of 40 kDa (as determined by sodium dodecyl sulfate polyacrylamide gel electrophoresis after the protein was prepared under reducing conditions, from a regression based on the log of the molecular weight of standard proteins), and an isoelectric point of 3.9 as determined by isoelectric focusing electrophoresis from a regression of distance versus isoelectric point of standard proteins. Conditions for molecular weight determination and isoelectric point determination are described in detail in patent application Ser. No. 07/919,784. It has an optimum pH for activity of about 3 to 7. The production and purification of this chitobiosidase are described in Harman et al U.S. Pat. No. 5,173,419 where it is referred to as a chitobiase and also in patent application Ser. No. 07/919,784, filed Jul. 27, 1992 where it is referred to as a chitobiase and also as a chitobiosidase. The enzyme obtained in Ser. No. 07/919,784 has a specific activity of 127 nkatal/mg protein and is purified to greater than a 200-fold increase in specific activity compared to its activity in the culture filtrate. Ser. No. 07/919,784 refers to the presence also of a minor band at 36 kDa. It has since been discovered that the chitobiosidase from Trichoderma harzianum strain P1 (ATCC 74058) gives three closely spaced protein bands with molecular weights of 40 kDa (staining most intensely), 38 kDa (faintest stain) and 35 kDa (intermediate intensity stain), as determined by sodium dodecyl sulfate polyacrylamide gel electrophoresis after the protein was prepared under reducing conditions, from a regression based on the log of the molecular weight of standard proteins, and that the three bands represent different levels of N-glycosylation of the same protein. The term "biologically pure" as used herein includes the 40 kDa enzyme isolated as described above with or without the same protein with different level of glycosylation also being present.

The N-acetyl-β-D-glucosaminidases cleave monomeric units from chitin from one end, i.e., release N-acetylglucosamine from chitin. N-Acetyl-β-D-glucosaminidases may be referred to for convenience hereinafter as glucosaminidases. Glucosaminidase activity is readily determined by measuring the release of p-nitrophenol from P-nitrophenyl-β-D-N-acetylglucosaminide, e.g., by the same procedure as described above for assaying for chitobiosidase activity except for the substitution of substrate. An activity of one nanokatal (nkatal) corresponds to the release of 1 nmol nitrophenol per second. Glucosaminidase activity is present in culture filtrates from *Trichoderma harzianum* strain P1 having accession No. ATCC 74058 and from *Gliocladium virens* strain 41 having accession No. ATCC 20906.

The β-1,3-glucanolytic enzymes include, for example, glucan 1,3-β-glucosidases. The glucan 1,3-β-glucosidases cleave 1,3-β-glucans. The sources for these enzymes are typically the same as the sources for chitinolytic enzymes and are preferably microorganisms from the genera Trichoderma and Gliocladium. Glucan 1,3-β-glucosidase activity is readily determined by measuring the amount of reducing sugar release from laminarin in a standard assay containing 250 μl of enzyme solution and 250 μl of a 0.1% solution of laminarin in 50 mM potassium phosphate buffer, pH 6.7, wherein incubation is carried out at 30° C. for 1 hour whereupon 250 μl of a copper reagent (prepared by dissolving 28 g $Na_2PO_4$ and 40 g potassium sodium tatrate in 700 ml deionized water, adding 100 ml of 1N NaOH, then adding 80 ml of a 10% (w/v) solution of $CuSO_4.5H_2O$ with stirring, then adding 180 g $Na_2SO_4$, when all the ingredients have dissolved, bringing to 1 L with deionized water, then allowing to stand for 2 days, then decanting and filtering) is added, and the admixture is covered with foil and heated for 20 minutes in a steam bath, whereupon, after cooling, 250 μl of arsenomolybdate reagent (prepared by dissolving 25 g of $(NH_4)_6Mo_7O_{24}.4H_2O$ in 450 ml deionized water, adding 21 ml concentrated $H_2SO_4$ with mixing, then adding a solution containing 3 g $Na_2HAsO_4.7H_2O$ in 25 ml distilled water and mixing, incubating at 37° C. for 2 days and storing in a brown bottle until used) is added with mixing, followed by adding 5 ml deionized water, and reading color in a spectrophotometer at 510 nm, and wherein appropriate controls without either enzyme or substrate may be run simultaneously; the quantity of reducing sugar is calculated from glucose standards included in the assay. An activity of one nkatal corresponds to the release of 1 nmol glucose equivalent per second. Glucan 1,3-β-glucosidase activity is present in culture filtrates from *Trichoderma harzianum* strain P1 having accession No. ATCC 74058 and from *Gliocladium virens* strain 41 having accession No. ATCC 20906.

A glucan 1,3-β-glucosidase is isolated from *Trichoderma harzianum* strain P1 having accession No. ATCC 74058 and has a molecular weight of 78 kDa (as determined by sodium dodecyl sulfate polyacrylamide gel electrophoresis after the protein was prepared under reducing conditions, from a regression based on the log of molecular weight of standard proteins) and an isoelectric point of 6.2 as determined by isoelectric focusing electrophoresis from a regression of distance versus the isoelectric point of standard proteins. The procedures for molecular weight determination and isoelectric point determination are the same as those described in Ser. No. 07/919,784. The enzyme has activity against β-1,3 glucan laminarin between pH 4 and 7, with the strongest activity between 4.5 and 5.5. The enzyme is obtained and purified as generally described above with the medium for culturing of the microorganism being SMCS medium (described in comparative Example 2 hereinafter). After the chromatofocusing step, several peaks with glucan 1,3-β-glucosidase activity are detected and fractions from major activity peaks are pooled, dialyzed, concentrated and applied to the Rotofor cell to obtain an electrophoretically pure exo-glucosidase. The production and purification of the enzyme are described in detail in the patent application of Harman et al, Ser. No. 07/990,609, filed on Dec. 15, 1992. The enzyme was purified to a specific activity 35-fold that of its activity in the culture filtrate.

The cellulases are enzymes which cleave cellulosic polysaccharides. Cellulase activity is readily measured by the reducing group assay described previously except that cellulose or a cellulose derivative is substituted for laminarin. Other assays are known to those skilled in the art. One nkatal of activity corresponds to the release of 1 nmol glucose equivalent per second.

Cellulases are produced, for example, by fungi of the genera Aspergillus, (e.g., *Aspergillus niger*), Trichoderma (e.g., *Trichoderma viride*) and Thielatia (e.g., *Thielatia terrestris*).

Combinations of the above-described enzymes are useful herein. A preferred combination is provided by endochitinase and chitobiosidase in a weight ratio ranging from 3:1 to 1:1.2, very preferably ranging from 2:1 to 1:1.

We turn now to the antifungal bacteria for use as component (b) of the composition herein. As indicated above, these bind to fungal cell walls in a 2% dextrose aqueous solution in the presence of enzyme (a), e.g., when fungal cells are cultured in potato dextrose broth in the presence of enzyme (a), but which do not bind to fungal cell walls in a 2% dextrose aqueous solution in the absence of enzyme (a), e.g., when fungal cell walls are cultured in potato dextrose broth without enzyme (a) present. Potato dextrose broth, when not further qualified, is used herein to mean the aqueous admixture formed by dissolving 24 g of a powder (obtained from Difco Laboratories, Detroit, Mich.) consisting of 20 g dextrose and 4 g solids, obtained from filtering and drying 200 g of infusion from potatoes, in 1 liter of water and sterilizing by autoclaving, final pH of 5.1±0.2. Preferably, the antifungal bacteria herein are selected from those of the genus Enterobacter and very preferably are not species which are pathogenic to humans or animals. Very preferred species of Enterobacter for use as antifungal bacteria (b) herein, include, for example, *Enterobacter cloacae*, *Enterobacter aerogenes*, *Enterobacter agglomerans*, *Enterobacter dissolvens*, *Enterobacter intermedius* and *Enterobacter sakazakii*. *Enterobacter cloacae* is most preferred. *Enterobacter cloacae* is a frequent organism in the spermosphere and rhizosphere of plants and is rhizosphere competent. *Enterobacter cloacae* strain E6 having accession No. ATCC 39978 is especially preferred. The antifungal bacteria (b) of the composition herein do not include *Pseudomonas fluorescens* and *Pseudomonas putida* which unlike the bacteria of (b) do not bind to fungal cell walls when enzyme (a) is absent even in the absence of the sugars D-glucose and sucrose or when cultured in potato dextrose broth in the presence of enzyme (a).

As indicated above, the enzyme (a) and bacteria (b) are present in a ratio of (b) to (a) ranging from 1 cell of (b) to 1 μg of (a) to 200,000 cells of (b) to 1 μg of (a). Preferably the enzyme (a) and bacteria (b) are in a ratio of (b) to (a) which is at least 3 cells of (b) to 1 μg of (a).

The compositions herein are readily formulated by admixing the fungal cell wall degrading enzymes and antifungal bacteria with non-toxic carriers appropriate for the particular use for the composition, e.g., agriculturally acceptable carriers for agricultural uses. They may be formulated as liquids (solutions or suspensions) or as solids. Suitable carriers include, for example, water, adhesives such as carboxymethylcellulose, methyl cellulose, gum arabic, and polyethylene glycol, talc, peat moss, simple carbohydrates and particulate cellulose. The carrier can also be a medium which supports the growth of bacteria (b), such as potato dextrose broth, Richard's medium, Czapek's broth or trypticase soy broth, or medium which is dissolvable or suspendible or reconstitutable to be such bacteria growth supporting medium. The enzyme (a) should be present in an amount effective for binding of bacteria (b) to fungal cell walls when D-glucose and/or sucrose is present. For liquid compositions, the enzyme component (a) is preferably present at a concentration ranging from 5 to 100 µg/ml, very preferably from 20 to 50 µg/ml for endochitinase, 50 to 75 µg/ml for chitobiosidase and 5 to 25 µg/ml for at 1:1 combination of chitobiosidase and endochitinase, depending on the target fungus, for in vitro uses. Concentrations for practical agricultural uses can differ according to application and delivery system and may range up to 10 times those listed above as preferred for in vitro uses.

We turn now to the method herein which is directed to inhibiting the replication, germination or growth of a fungus and comprises contacting such fungus, or a locus to be protected from such fungus, with an antifungal effective amount of appropriate composition herein.

In its broad aspect, the method utilizing composition herein comprises contacting the target fungus, or a locus to be protected from such fungus, with a composition comprising (a) purified fungal cell wall degrading enzyme, and (b) antifungal bacteria as broadly described above, in a ratio of (b) to (a) ranging from 1 cell of (b) to 1 µg of (a) to 200,000 cells of (a) to 1 µg of (a), with the combination of (a) and (b) being present in an antifungal effective amount.

Preferably, the method utilizing the composition herein comprises contacting the target fungus, or a locus to be protected from such fungus, with a composition comprising purified fungal cell wall degrading enzyme (a) selected from the group consisting of endochitinase isolated from *Trichoderma harzianum* strain P1 having accession No. ATCC 74058, chitin 1,4-β-chitobiosidase isolated from *Trichoderma harzianum* strain P1 having accession No. ATCC 74058 and combinations thereof, and antifungal bacteria (b) which are *Enterobacter cloacae* strain E6 having accession No. ATCC 39978, in a ratio of (b) to (a) ranging from 3 cells of (b) to 1 µg of (a) to 200,000 cells of (b) to 1 µg of (a), with the combination of (a) and (b) being present in an antifungal effective amount.

For agricultural purposes, application of antifungal composition can be to seeds, foliage, roots or fruit to be protected or to the soil surrounding a plant or seed to be protected, or to fungus thereon which is to be inhibited. Normally application is topical.

The method of use herein utilizes compositions containing fungal cell wall degrading enzymes (a), which are chitinolytic enzymes or β-1,3-glucanolytic enzymes, for application to fungi containing, as major structural components, chitin and β-1,3-glucan, e.g., species from genera including Fusarium, Gliocladium, Rhizoctonia, Trichoderma, Uncinula, Ustilago, Erysiphe, Botrytis, Saccharomyces, Sclerotium and Alternaria. Example I hereinafter is directed to application to species from the genera Fusarium, Uncinula and Botrytis, which were selected in the work supporting this invention as model test fungi.

The method of use herein utilizes compositions containing fungal cell wall degrading enzymes (a) which are cellulases for application to lower fungi (i.e., Oomycetes) where the cell walls contain, as major structural component, cellulosic polysaccharides, e.g., species from the genera Pythium and Phytophthora.

In the composition herein and in the method of its use, interaction is provided between the cell wall degrading enzyme component and the antifungal bacteria component to increase the potency of the antifungal bacteria against pathogenic fungi and so that the antifungal bacteria bind to fungal cell walls even in the presence of sucrose and D-glucose to expand the range of use to seeds and plants which excrete these sugars.

We turn now to the method herein for causing proliferation in the growth of *Enterobacter cloacae* which comprises the steps of reacting fungal cell wall degrading enzyme with a substrate therefor to obtain a nutrient for *Enterobacter cloacae* and growing *Enterobacter cloacae* in the presence of said nutrient so as to cause said proliferation. In the case of all substrates, the nutrient is made up of monosaccharide and/or oligosaccharide hydrolysis product. When the substrate is a fungus, the nutrient additionally contains cytoplasm (including lipids, proteins, carboxhydrates and nucleic acids) released from the substrate by action thereon of the cell wall degrading enzyme.

In this method, the cell wall degrading enzymes are the same as those described for component (a) above except that the enzymes can be used in purified or natural form, i.e., not separated from the source (e.g., by utilizing source microorganisms in the composition herein). Even with this breadth, the method is not found in nature as indicated by the results of Example III wherein the control medium (*E. cloacae* and no substrate for enzyme) produced about the same or greater growth of *E. cloacae* as where *E. cloacae* and substrate for enzyme, but no added enzyme, were present.

The substrates for the chitinolytic enzymes include moist purified colloidal chitin and for the β-1,3-glucanolytic enzymes include laminarin and for chitinolytic and β-1,3-glucanolytic enzymes include living hyphae of Fusarium, Gliocladium, Rhizoctonia, Trichoderma, Uncinula, Ustilago, Erysiphe, Botrytis, Saccharomyces, Sclerotium and Alternaria. The substrates for cellulases include species from the genera Pythium and Phytophthora.

The reaction of cell wall degrading enzyme and substrate therefor is preferably carried out in a growth supporting medium for *Enterobacter cloacae*, e.g., potato dextrose broth, Richard's medium, Czapek's broth or trypticase soy broth. The reaction is carried out by utilizing substrate in a nutrient producing amount, e.g., 10 to 30 mg chitin, preferably 20 mg chitin, per ml of medium or $1 \times 10^4$ to $5 \times 10^6$ conidia of fungal substrate per µl of medium. The reaction is preferably carried out by utilizing cell wall degrading enzyme at a concentration of 1 to 500 µg per ml of medium and incubating for 24 to 30 hours at 25° to 30° C. Monosaccharide and oligosaccharide hydrolysis product, and when hyphae constitute substrate, also released cytoplasm, are preferably recovered, e.g., by centrifuging and filtering, and retaining the filtrate, and *E. cloacae* is preferably grown in the presence of the said filtrate by incubating for 24 to 48 hours at 25° to 30° C. at greater than 80% relative humidity.

The invention is illustrated in the following examples.

In the Examples, the following applies. The results are the average between at least two experiments with three replicates for each experiment. The standard deviations were calculated from at least two experiments. For the analysis of spore germination, the values obtained for the control were taken as 0% inhibition, and all other values were divided by these values and multiplied by 100 to obtain percent of inhibition. Limpel's formula as described by Richer, D. L., Pestic. Sci. 19:309–315 (1987) was used to determine antifungal synergistic interactions. This formula is $E_e = X + Y - XY/100$ where $E_e$ is the expected effect from the additive responses of two inhibitory agents, and in the present case, X and Y are the percentages of inhibition relative to each agent used alone, and a value greater than $E_e$ indicates synergism exists.

EXAMPLE I

This experiment involved determining any synergistic effect obtained in inhibiting conidia germination and germ tube elongation of *Botrytis cinerea, Fusarium solani* and *Uncinula necator* by combination of endochitinase described hereinbefore which is isolated from *Trichoderma harzianum* strain P1 having accession No. ATCC 74058, chitin 1,4-β-chitobiosidase described hereinbefore having a molecular weight of 40 kDa and an isoelectric point of 3.9 which is isolated from *Trichoderma harzianum* strain P1 having accession No. ATCC 74058, or a 1:1 weight mixture of these enzymes, and *Enterobacter cloacae* strain E6 having accession No. ATCC 39978, *Pseudomonas fluorescens* strain TL-3 (Burr, T. J., et al, Phytopathology 68, pages 1377–1383, 1978) or *Pseudomonas putida* strain BK-1 (Burr, T. J., et al, Phytopathology 68, pages 1377–1383, 1978).

Conidia of *B. cinerea* and *F. solani* were grown at 20°–25° C. on potato dextrose agar (Difco Laboratories, Detroit, Mich.), suspended in water, filtered through sterile Kimwipes (Kimberly-Clark, Roswell, Ga.).

Conidia of *U. necator* were produced on grapes grown aseptically in tissue culture, suspended in 0.4 osmol mannitol, filtered through sterile Kimwipes.

Cells of *E. cloacae* strain E6 (ATCC 39978) were grown in potato dextrose broth at 28°–30° C. on a rotary shaker at 200 rpm to mid log phase (optical density of 600 nm=0.4 to 0.6), harvested by centrifugation, washed in 0.85% NaCl solution and resuspended in sterile water for the bioassays.

Cells of the Pseudomonas spp were grown in King's Medium B at 28°–30° C. on a rotary shaker at 200 rpm to mid log phase (optical density of 600 nm=0.4 to 0.6), harvested by centrifugation, washed in sterile water and resuspended in sterile water for the bioassays.

Enzyme solutions were kept at 4° C. and utilized for the bioassays within two weeks. Otherwise they were concentrated to dryness in a SpeedVac apparatus (Savant Instruments, Farmingdale, N.Y.) and stored at −20° C. until dissolved to provide solutions for the bioassays.

Test solutions or suspensions were prepared that contained in sterile water either a single enzyme, a 1:1 mixture of the two enzymes, bacterial cells from a single strain or enzyme(s) and bacterial cells from a single strain, and sterile water was used as a control.

The enzyme solutions were made up to provide in an assay a concentration of enzyme(s) with an $ED_{20-30}$ for spore germination for the test fungus participating in the assays (i.e., a dose effective to inhibit 20% to 30% of spore germination). The enzyme concentrations for the assays for *U. necator, F. solani* and *B. cinerea* were respectively 50, 75 and 50 μg ml$^{-1}$ for the chitobiosidase, 25, 50 and 25 μg ml$^{-1}$ for the endochitinase and 9, 25 and 8 μg ml$^{-1}$ for the total protein constituting the 1:1 mixture of the chitobiosidase and the endochitinase. Since the enzyme test solution constituted one-third of an assay mixture, the enzyme test solutions were made up at 3 times the strength desired in the assays.

The test suspensions of bacterial cells were made up to initially contain 1.5 to 2.5×10$^4$ bacterial cells ml$^{-1}$ so as to provide 300–500 bacterial cells in an assay mixture. For *E. cloacae*, this amount of cells produced about 30% inhibition of the spore germination for all of the test fungi and 45 to 50% inhibition of germ tube elongation for all of the test fungi. Increasing or decreasing the initial inoculation for *E. cloacae* proportionally affected the level of inhibition, except that the highest level of inhibition of spore germination that could be obtained by increasing the initial inoculum of *E. cloacae* was 65%. For the Pseudomonas spp., the highest level of inhibition of spore germination that could be obtained by increasing the initial inoculum was not more than 10%.

Suspensions of test fungus containing 10$^6$–10$^7$ conidia ml$^{-1}$ were made up for the assays.

Additionally a potato dextrose broth solution was made up of strength three times that to be present in the assay mixtures as medium for the assays.

For the assays, 20 μl of test solution or control, 20 μl of conidia suspension and 20 μl of potato dextrose broth solution medium were admixed in a sterile Eppendorf tube. The tubes were incubated at 25° C., and after 24 to 30 hours, the percentage of germinating conidia for each tube (percentage of the first 100 spores seen on a microscope slide), and the lengths of 20 germ tubes were measured and averaged. Percent inhibition of spore germination was calculated according to the following equation: $\%I = (1 - \%S_t/\%S_c) \times 100$, where %I represents the percentage inhibition, $\%S_t$ represents percentage germination of spores in the treatment of interest, and $\%S_c$ represents the percentage germination of spores in the control (i.e., with neither antifungal bacteria nor enzyme). A similar equation was used to calculate inhibition of germ tube elongation, except that germ tube length in μm for treatment of interest and for the control were respectively substituted for $\%S_t$ and $\%S_c$.

Figure 1B:
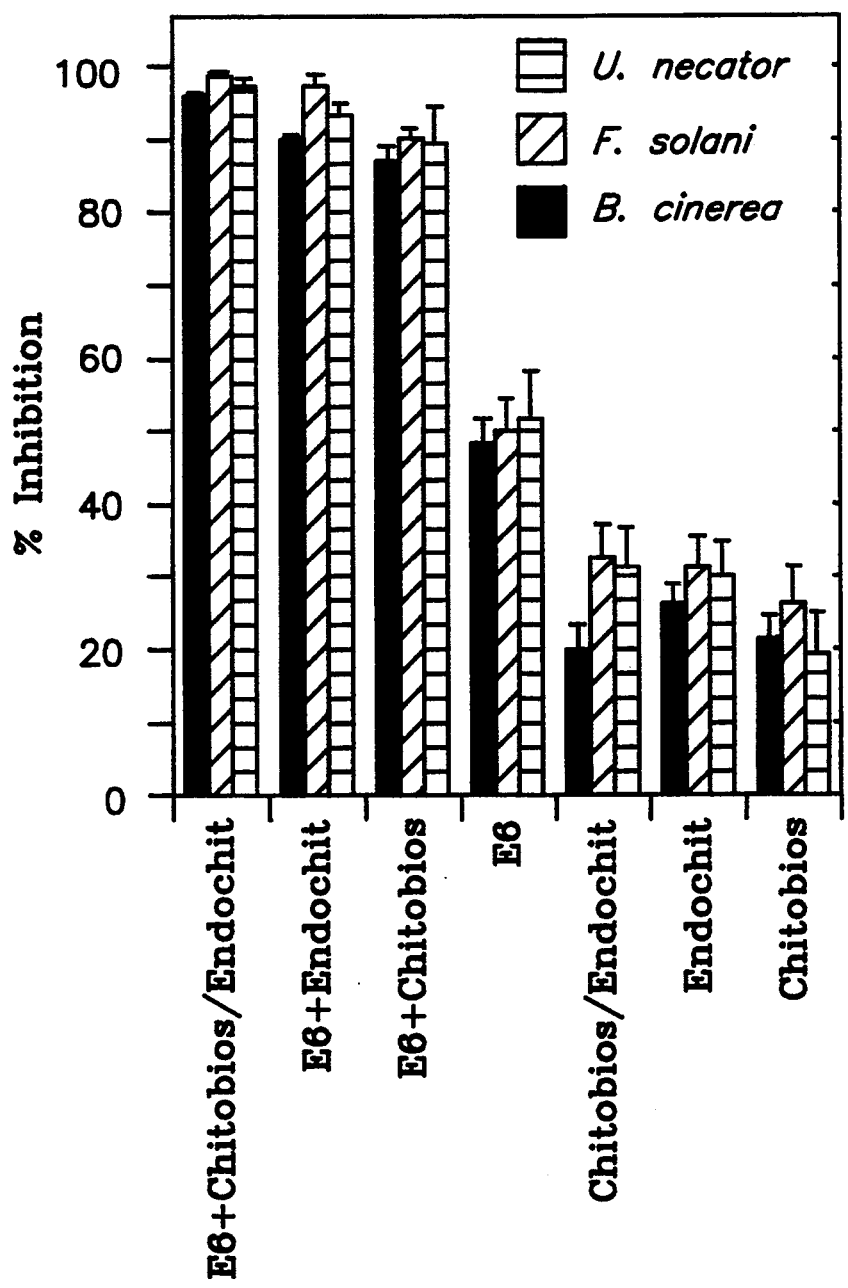
FIG. 1B is a set of bar graphs depicting percent inhibition of germ tube elongation for various treatments of three fungi and sets forth results of Example I.

Results are set forth in FIGS. 1A and 1B.

FIGS. 1A and 1B are sets of bar graphs depicting % inhibition for enzymes, *E. cloacae* and the combination of enzymes and *E. cloacae*, in respect to the three target fungi, respectively of spore germination and germ tube elongation. In FIGS. 1A and 1B, the solid black bars represent assays involving *B. cinerea*, the diagonally hatched bars represent assays involving *F. solani* and the horizontally hatched bars represent assays involving *U. necator* and "E6" means *E. cloacae* strain E6, "Chitobios" means the chitobiosidase described in this example, "Endochit" means the endochitinase described in this example and "Chitobios/Endochit" means the 1:1 mixture of chitobiosidase and endochitinase described in this example. In FIGS. 1A and 1B, the error bars indicate standard deviations.

The data of FIGS. 1A and 1B demonstrates synergy according to Limpel's formula.

Turning firstly to FIG. 1A, even assuming 30% inhibition of spore germination for enzyme alone and for *E. cloacae* alone in the case of each fungus, Limpel's formula gives 30+30−30(30)/100 which equals 51. Even if the effect of *E. cloacae* is maximized by increasing the initial inoculum to provide 65% inhibition, Limpel's formula gives 65+30−65(30)/100 which equals 75.5. However, as shown in FIG. 1A, the combination even without increased inoculum of E. cloacae provides levels of inhibition close to 100%, thereby demonstrating synergy.

Turning now to FIG. 1B and considering it as showing 30% inhibition of germ tube elongation for enzyme alone and 50% inhibition of germ tube elongation for E. cloacae alone, Limpel's formula gives 65%. On the other hand, the result shown for the combination is about 90% inhibition or more, thereby demonstrating synergy.

In summary, when E. cloacae or enzyme was added to the target fungi alone, there was some effect. However, when enzyme and E. cloacae were combined, the target fungi were largely destroyed; spore germination was reduced to very low levels, and the surviving germ tubes grew poorly. Furthermore, synergy was evident with the combination of either or both enzymes and E. cloacae.

The addition of cells of Pseudomonas spp to samples containing either of the enzymes from T. harzianum strain P1 or combination thereof, did not increase the level of inhibition for any fungus tested. This demonstrates that the synergistic result is not obtained when antifungal bacterium which does not bind to fungal cell walls is substituted for the E. cloacae (which as shown in Example III binds to fungal cell walls in the presence of cell wall degrading enzyme even when interfering sugars are present).

COMPARATIVE EXAMPLE 1

Cells of E. cloacae strain E6 (ATCC 39978) were grown on potato dextrose broth at 28°–30° C. on a rotary shaker at 200 rpm until mid to late log phase was reached (optical density at 600 nm of 0.7 to 1.0). The culture filtrate was harvested by centrifugation, filtered through a 0.45 μm pore size filter, dialyzing the filtrate against distilled water overnight at 4° C. and concentrating by dialysis (6–8 kDa cutoff) about 20- to 25-fold using polyethylene glycol (35,000 MW, Fluka Chemika Biochemika, Buchs, Switzerland).

Test solutions were made up of the dialyzed, concentrated culture filtrate, with and without enzymes (chitobiosidase, endochitinase and a 1:1 mixture of chitobiosidase and chitobiase as in Example I).

Suspensions of conidia of B. cinerea, F. solani and U. necator were made up as in Example I.

Potato dextrose broth solution of three times strength was made up as in Example I.

Assays were carried out as in Example I except that culture filtrate from E. cloacae was utilized in place of living bacteria.

No synergistic antifungal effect was noted for the combinations of E. cloacae culture filtrate and enzymes from T. harzianum strain P1 against any of the test fungi.

For example, with culture filtrate alone, 21% inhibition of spore germination of B. cinerea was obtained. For endochitinase alone at 25 μg ml$^{-1}$ in the assay, 28% inhibition of spore germination of B. cinerea was obtained. For the combination, 38% inhibition was obtained. Substituting 21 and 28 in Limpel's formula gives 43%. Thus, no synergy was present. The above indicates that the presence of intact bacterial cells is required for a synergistic effect rather than extracellular metabolite thereof.

EXAMPLE II

Figure 2:
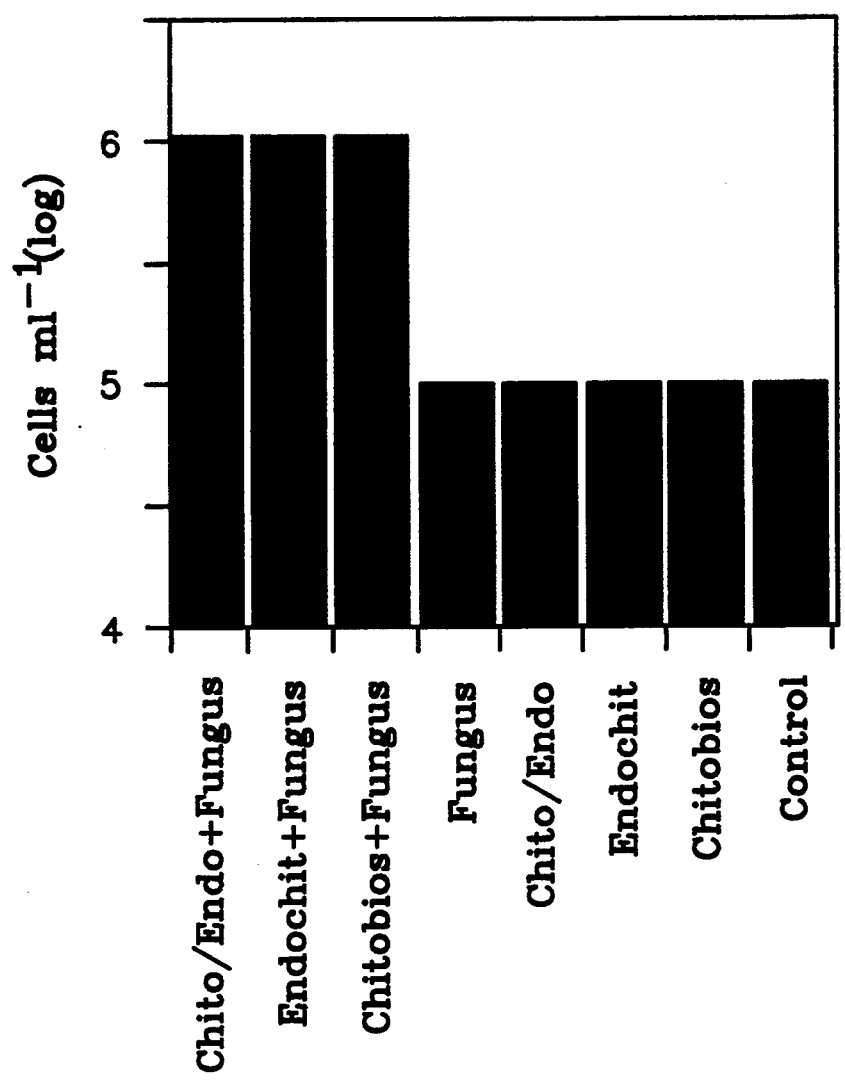
FIG. 2 is a set of bar graphs depicting amount of *E. cloacae* cells determined for various treatments (test solutions) and sets forth results of Example II.

Assays were carried out as in Example I except that E. cloacae cell density was determined rather than % inhibition. The cell density was determined for bacterial cells not in clusters and was carried out microscopically using a Petroff-Hauser counting chamber. Results are shown in FIG. 2 which is a set of bar graphs depicting amount of E. cloacae cells determined for the various test solutions. In FIG. 2, "Chitobios" means chitobiosidase, "Endochit" means endochitinase, "Chito/Endo" means a 1:1 mixture of endochitinase and chitobiase, fungus means B. cinerea, F. solani or U. necator (results were similar for the test fungi) and "Control" means sterile water. As shown in FIG. 2, the density of cells of E. cloacae not associated in clusters was about 10-fold higher in samples containing test fungus and chitinolytic enzymes, compared to controls without enzyme and/or fungus. This shows that chitinolytic enzyme in the presence of substrate (in this case the fungus) stimulated the replication of E. cloacae.

EXAMPLE III $1 \times 10^6$ conidia of test fungi or 2% moist purified chitin (prepared as described in Vessey, J. C., et al, Trans. Br. Mycol. Soc. 60:133–143, 1973 by grinding and washing crab shell chitin with distilled water, and then with a mixture containing ethanol:diethyl ether:HCl, 50:50:1, precipitating by diluting with ice water, and then repeatedly washing with water adjusted to pH 8.5 until the pH of the chitin equals at least 3) were placed in 200 μl potato dextrose broth in sterile Eppendorf tubes at 25° C., and after 24 hours endochitinase from T. harzianum strain P1 and/or the 40 kDa chitobiosidase from T. harzianum strain P1 were added to the tubes at a final concentration of 50 μg ml$^{-1}$ for endochitinase and 100 μg ml$^{-1}$ for chitobiosidase. Control samples contained medium, substrate and sterile water instead of enzyme or medium, enzyme and sterile water instead of substrate or only medium. After this addition the tubes were reincubated at 25° C. After 24 hours, all samples were centrifuged and the supernatant was recovered and filtered through a 0.45 μm pore size polysulfone filter. For each sample, one hundred μl of the resulting filtrate was placed in a well of a standard ELISA plate containing about 500 cells of E. cloacae strain E6 suspended in 10 μl of potato dextrose broth. For each sample, the absorbance at 560 nm was determined initially. Then each plate was incubated at 30° C. over moistened towels to maintain high relative humidity. Bacterial growth was monitored at 24, 29 and 48 hours by measuring the absorbance at 560 nm and subtracting the initial value from the readings obtained.

Results for 29 hours are set forth in FIG. 3 which is a set of bar graphs depicting change in absorbance for various substrates and enzymes.

As shown in FIG. 3, after 29 hours, the absorbance at 560 nm was much higher in samples containing a chitinous substrate (chitin or fungi) in the presence of chitinolytic enzymes compared with a control medium or with controls containing a substrate incubated without enzyme or enzyme incubated without a substrate, indicating a much higher bacterial cell density where enzyme and substrate were present. Differences in bacterial cell density between samples were also confirmed microscopically in a Petroff-Hauser counting chamber.

The results suggest that the enzymes released sufficient nutrients from the substrates (chitin and fungi) to proliferate the E. cloacae to high levels.

EXAMPLE IV

Young hyphae of B. cinerea in potato dextrose broth supplemented with 100 mM sucrose were inoculated with cells of E. cloacae strain E6 in the absence of enzyme. The E. cloacae cells did not bind to the B. cinerea hyphae.

In one case endochitinase from T. harzianum strain P1 at 50 μg ml$^{-1}$ and in a second case the 40 kDa chitobiosidase from T. harzianum strain P1 at 75 μg ml$^{-1}$ were added. Binding of the E. cloacae cells to the B. cinerea starts to occur within 2 to 5 hours and occurs in almost all cases within 4 to 5 hours. The binding is coincident with a great increment in antifungal activity.

COMPARATIVE EXAMPLE 2

E. cloacae strain E6 bacteria were grown for 3 days at 28° to 30° C. to mid to late log phase (optical density at 600 nm=0.7 to 1.0) in 250 ml of SMCS medium (680 mg $KH_2PO_4$, 870 mg $K_2HPO_4$, 200 mg KCl, 1 g $NH_4NO_3$, 200 mg $CaCl_2$, 200 mg $MgSO_4.7H_2O$, 2 mg $FeSO_4$, 2 mg $ZnSO_4$, 2 mg $MnSO_4$, 42 g moist colloidal chitin prepared as described in Example III, in 1 L distilled water, final pH 6.0) and in another case in SMS medium (same as SMCS medium but with 5 g sucrose substituted for colloidol chitin). The culture filtrate was harvested by centrifugation and filtration through a 0.45 μm pore size filter and the filtrate was dialyzed against distilled water overnight at 4° C., and then concentrated by dialysis (6–8 kDa cutoff) about 20- to 25-fold using polyethylene glycol (35,000MW; Fluka Chemika-Biochemika, Buchs, Switzerland) and assayed for enzyme activity. No chitobiosidase, glucosaminidase or glucanase activity was detected. A low level of endochitinase activity was detected; 500 μl of the dialyzed concentrated culture filtrate reduced the turbidity of a suspension of colloidal chitin 28% when the bacteria were grown on SMCS medium and 14% when the bacteria were grown on SMS medium.

As indicated in FIG. 3, the endochitinase activity produced by E. cloacae is not such as to provide synergy as indicated by comparison of results for control medium with those for substrate (chitin or fungi).

As indicated in Example IV, the endochitinase activity produced by E. cloacae is not such as to effect binding to fungal hyphae when interfering sugars are present.

Variations of the invention will be obvious to those skilled in the art.

For example, genes coding for chitinolytic enzymes can be added to bacteria that adhere to fungal cell walls (in the absence of interfering sugars but not in the presence of D-glucose and sucrose) so that resulting transgenic bacteria produce chitinolytic enzymes thereby to provide potent control of pathogenic fungi and protect plant seeds regardless of level of carbohydrates exuded during seed germination.

Therefore, the invention is defined by the claims.

What is claimed is:

1. An antifungal composition comprising
   (a) purified fungal cell wall degrading enzyme selected from the group consisting of endochitinases, chitin 1,4-β-chitobiosidases, N-acetyl-β-D-glucosaminidases, and combinations thereof, and
   (b) these being present in a ratio of (b) to (a) ranging from 200 cells of (b) to 1 μg of (a) to 200,000 cells of (b) to 1 μg of (a),
   the combination of (a) and (b) being present in an antifungal effective amount and demonstrating antifungal synergistic interaction in accordance with Limpel's formula.

2. The antifungal composition of claim 1 wherein (a) and (b) are present in a concentration where individually they would give about 20 to 60% fungal inhibition.

3. The antifungal composition of claim 2 wherein (a) is present in a concentration where it individually would give about 20 to 40% fungal inhibition and (b) is present in a concentration where it individually would give about 30 to 60% fungal inhibition.

4. The antifungal composition of claim 3 wherein the fungal cell wall degrading enzyme is obtained from Trichoderma harzianum strain P1 having accession No. ATCC 74058.

5. The antifungal composition of claim 3 wherein the fungal cell wall degrading enzyme is selected from the group consisting of endochitinases and chitin 1,4-β-chitobiosidases and combinations thereof.

6. The antifungal composition of claim 3 wherein the fungal cell wall degrading enzyme is selected from the group consisting of endochitinase isolated from Trichoderma harzianum strain P1 having accession No. ATCC 74058, chitin 1,4-β-chitobiosidase isolated from Trichoderma harzianum strain P1 having accession No. ATCC 74058 and combinations thereof, and the antifungal bacteria are Enterobacter cloacae strain E6 having accession No. ATCC 39978.

7. A method for inhibiting the replication, germination or growth of a chitin-containing fungus, which comprises contacting such fungus or a locus to be protected from such fungus, with an antifungal effective amount of the composition of claim 1.

8. A method of inhibiting the replication, germination or growth of a chitin-containing fungus, which comprises contacting such fungus or a locus to be protected from such fungus, with an antifungal effective amount of the composition of claim 6.

9. A method for causing proliferation in the growth of Enterobacter cloacae, said method comprising the steps of reacting fungal cell wall degrading enzyme with substrate therefor to obtain a nutrient for Enterobacter cloacae and growing Enterobacter cloacae in the presence of said nutrient so as to cause said proliferation, said fungal cell wall degrading enzyme being selected from the group consisting of endochitinases, chitin 1,4-β-chitobiosidases, N-acetyl-β-D-glucosaminidases, and combinations thereof.

10. The method of claim 9 wherein the fungal cell wall degrading enzyme is purified enzyme.

11. The method of claim 10 wherein the fungal cell wall degrading enzyme is selected from the group consisting of endochitinases and chitin 1,4-β-chitobiosidases and combinations thereof.

12. The method of claim 11 wherein the fungal cell wall degrading enzyme is obtained from the group consisting of endochitinase isolated from Trichoderma harzianum strain P1 having accession No. ATCC 74058, chitin 1,4-β-chitobiosidase isolated from Trichoderma harzianum strain P1 having accession No. ATCC 74058 and combinations thereof.

* * * * *

UNITED STATES PATENT AND TRADEMARK OFFICE
CERTIFICATE OF CORRECTION

PATENT NO. : 5,360,608
DATED : November 1, 1994
INVENTOR(S) : Gary E. Harman et al It is certified that error appears in the above-identified patent and that said Letters Patent is hereby corrected as shown below:

Title page, item [54] line 4, and col. 1, line 3, IN THE TITLE, change "STIMULATION" to -- STIMULATING --.

Claim 1 (column 14, line 3), after "(b)" insert -- *Enterobacter cloacae* -- and move "these being present in a ratio of (b) to (a) ranging" to a line below but above what is column 14, line 4.

Signed and Sealed this

Third Day of January, 1995

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,360,608

DATED : November 1, 1994

INVENTOR(S) : Gary E. Harman et al

It is certified that error appears in the above-identified patent and that said Letters Patent is hereby corrected as shown below:

On the title page, item [54] and in column 1, line 3, in the title change "CLOACASE" to --CLOACAE--.

Signed and Sealed this

Fourteenth Day of February, 1995

*Attest:*

BRUCE LEHMAN

*Attesting Officer*  *Commissioner of Patents and Trademarks*